(12) United States Patent
Noelle et al.

(10) Patent No.: US 8,679,501 B2
(45) Date of Patent: Mar. 25, 2014

(54) METHOD FOR MODULATING INFLAMMATORY RESPONSES

(75) Inventors: Randolph J. Noelle, Plainfield, NH (US); Li-Fan Lu, Seattle, WA (US); Cory L. Ahonen, Enfield, NH (US)

(73) Assignee: Trustees of Dartmouth College, Hanover, NH (US)

( * ) Notice: Subject to any disclaimer, the term of this patent is extended or adjusted under 35 U.S.C. 154(b) by 205 days.

(21) Appl. No.: 12/090,369

(22) PCT Filed: Nov. 1, 2006

(86) PCT No.: PCT/US2006/060427
§ 371 (c)(1),
(2), (4) Date: Apr. 16, 2008

(87) PCT Pub. No.: WO2007/056642
PCT Pub. Date: May 18, 2007

(65) Prior Publication Data
US 2008/0220006 A1      Sep. 11, 2008

Related U.S. Application Data

(60) Provisional application No. 60/732,733, filed on Nov. 2, 2005.

(51) Int. Cl.
*A61K 39/395* (2006.01)
*A61K 39/00* (2006.01)
*A61K 39/38* (2006.01)

(52) U.S. Cl.
USPC .................................... 424/145.1; 424/184.1

(58) Field of Classification Search
None
See application file for complete search history.

(56) References Cited

U.S. PATENT DOCUMENTS

2001/0033839 A1 * 10/2001 Barbera-Guillem ....... 424/130.1

FOREIGN PATENT DOCUMENTS

WO   WO 2004091510 A2 * 10/2004

OTHER PUBLICATIONS

Kursar et al., 2002, J. Exp. Med. vol. 196: 1585-1592.*
Yarkoni et al., 1978, Infection and Immunity. vol. 21: 1029-1032.*
Yankai et al., 2006, Biochem and Bhiophys Res. comm. vol. 345: 1365-1371.*
Theoharides et al., 2004, Trends in Immunol. vol. 25: 235-241.*
Chen et al., "Conversion of peripheral CD4+ CD25−naive T cells to CD4+CD25+ regulatory T cells by TGF-β induction of transcription factor *Foxp3*", The Journal of Experimental Medicine 2003 198(12):1875-1886.
Corti et al., "Potential of real-time PCR assessment of granzyme B and perforin up-regulation for rejection monitoring in intestinal transplant recipients", Transplantation Proceedings 2005 37:4467-4471.
Gilliet et al., "Generation of human CD8 T regulatory cells by CD40 ligand-activated plasmacytoid dendritic cells", J. Exp. Med. 2002 195(6):695-704.
Graca et al., "Identification of regulatory T cells in tolerated allografts", J. Exp. Med. 2002 195(12):1641-1646.
Hara et al., "IL-10 is required for regulatory T cells to mediate tolerance to alloantigens in vivo¹", The Journal of Immunology 2001 166:3789-3796.
Kuppner et al., "The role of heat shock protein (hsp70) in dendritic cell maturation:Hsp70 induces the maturation of immature dendritic cells but reduces DC differentiation from monocyte precursors", Eur. J. Immunol. 2001 31:1602-1609.
Pilette et al., "IL-9 inhibits oxidative burst and TNF-α release in lipopolysaccharide-stimulated human monocytes through TGF-β¹", Journal Immunology 2002 168:4103-4111.
Robinson et al., "Tregs and allergic disease", Journal of Clinical Investigation 2004 114(10):1389-1397.
Shimizu et al., "Stimulation of CD25+CD4− regulatory T cells through GITR breaks immunological self-tolerance", Nature Immunology 2002 3(2):135-142.
Tarleton et al., "New approaches in vaccine development for parasitic infections", Cellular Microbiology 2005 7(10):1379-1386.
Tone et al., "Mouse glucorticoid-induced tumor necrosis factor receptor ligand is costimulatory for T cells", Proc. Natl. Acad. Sci. USA 2003 100 (25):15059-15064.
Townsend et al., "IL-9-deficient mice establish fundamental roles for IL-9 in pulmonary mastocytosis and goblet cell hyperplasia but not T cell development", Immunity 2000 13:573-583.
Zelenika et al., "The role of CD4+ T-cell subsets in determining transplantation rejection or tolerance", Immunological Reviews 2001 182:164-179.
Zhou et al., "Oral exposure to alloantigen generates intragraft CD8+ regulatory cells", Journal of Immunology 2001 167:107-113.
Zhou et al., "Th2 cytokines and asthma interleukin-9 as a therapeutic target for asthma", Respir Res 2001 22:80-84.

* cited by examiner

*Primary Examiner* — Amy Juedes
(74) *Attorney, Agent, or Firm* — Licata & Tyrrell P.C.

(57) ABSTRACT

The present invention is a method for inhibiting $T^{reg}$ cell functional activities by blocking $T^{reg}$ cell-mediated mast cell activation. It has been found IL-9 produced by $T^{reg}$ cells activates mast cells, which in turn mediate an amplification loop critical for graft tolerance and immune responses to tumors. Thus, a method for enhancing an immune response to a vaccine, such as a cancer vaccine, is also provided as is a method for increasing cell and humoral immunity in a subject.

1 Claim, 6 Drawing Sheets

METHOD FOR MODULATING INFLAMMATORY RESPONSES

INTRODUCTION

This application is a National Phase Application of International Application Number PCT/US2006/060427 filed Nov. 1, 2006, which claims priority to U.S. Provisional Ser. No. 60/732,733 filed Nov. 2, 2005, each of which are herein incorporated by reference in their entireties.

This invention was made in the course of research sponsored by the National Institutes of Health (Grant No. R01 AI048667). The U.S. government may have certain rights in this invention.

BACKGROUND OF THE INVENTION

CD40 is a 48 kDa transmembrane glycoprotein cell surface receptor that shares sequence homology with the tumor necrosis factor alpha (TNFα) receptor family and was initially identified as a B-cell surface molecule that induced B-cell growth upon ligation with monoclonal antibodies (Durie, et al. (1994) *Immunology Today* 15:406-411; Vogel & Noelle (1998) *Semin. Immunol.* 10:435-442; Banchereau, et al. (1994) *Ann. Rev. Immunol.* 12:881-922). Dendritic cells, macrophages, epithelial cells, hematopoietic progenitors, and non-hematopoietic cells have been shown to express CD40. Its ligand, CD154, is a 34-39 kDa type II integral membrane protein expressed on activated but not resting T cells, activated B cells (Higuchi, et al. (2002) *J. Immunol.* 168:9-12), and activated platelets (Henn, et al. (1998) *Nature* 391:591-594; Danese, et al. (2003) *Gastroenterology* 124:1249-1264). During inflammatory responses, other cell types such as peripheral blood monocytes, human vascular endothelial cells, smooth muscle cells and mononuclear phagocytes (Bavendiek, et al. (2002) *J. Biol. Chem.* 277:25032-25039) have all been shown to express CD154.

Blocking CD154 ligand, and thus CD40/CD154 ligation, is an effective means by which to induce transplantation tolerance (Montgomery, et al. (2001) *Immunol. Rev.* 183:214-222; Yamada & Sayegh (2002) *Transplantation* 73:S36-39). Prevention of transplant rejection by blocking CD40/CD154 interactions has been repeatedly documented for the induction of long-term tolerance to skin (Quezada, et al. (2003) *Blood* 102:1920-1926; Elster, et al. (2001) *Transplantation* 72:1473-1478; Gordon, et al. (1998) *Diabetes* 47:1199-1206; Markees, et al. (1997) *Transplantation* 64:329-335; Jarvinen, et al. (2003) *Transplantation* 76:1375-1379; Quezada, et al. (2004) *Annu. Rev. Immunol.* 22:307-328), islets (Benda, et al. (2002) *Cell Transplant.* 11:715-720), bone marrow (Wekerle, et al. (2001) *J. Immunol.* 166:2311-2316), and a myriad of other transplanted organs (Camirand, et al. (2002) *Transplantation* 73:453-461; Tung, et al. (2003) *Transplantation* 75:644-650). These findings demonstrate the importance of this receptor-ligand pair in immunity and tolerance.

Peripheral tolerance is a constitutive process, whereby the immune system is constantly generating active suppressive immune responses to self in the periphery. Successful induction of peripheral tolerance relies on the quiescent state of self-antigen presenting antigen presenting cells, provision of self-antigens in the appropriate macromolecular form, and the emergence of regulatory T-cells to appropriate self-specificities. Through understanding these mechanisms, successful strategies have been developed to induce tolerance to alloantigens for the purpose of inducing transplant tolerance. CD154 blockade alone and more commonly with other immunosuppressive interventions, can markedly delay graft rejection. It is widely held that one of the major effects of CD154 blockade is the interference with dendritic cell maturation. T-cell activation is inextricably linked to dendritic cell maturation based on the understanding of the signals that are necessary to induce T-cell expansion and differentiation. The two signal hypothesis of T-cell activation is an accepted paradigm that describes the early requirements for T-cell activation versus anergy (Mondino, et al. (1996) *Proc. Natl. Acad. Sci. USA* 93:2245-2252). This paradigm states that the proficient induction of an immune response requires T-cell receptor and MHC/peptide interaction (signal one) followed by the interaction between co-stimulatory molecules, namely CD80/86 and CD28 (signal two), and a possible myriad of other molecules. If signal one is generated in absence of signal two, the outcome is not immunity, but tolerance. Providing signal one and signal two becomes the responsibility of the antigen presenting cell, which must efficiently engage and trigger multiple T-cell surface molecules. To achieve this proficiency, antigen presenting cells must mature. Dendritic cell maturation by CD154 is unique in that it provides a spectrum of signals that trigger the upregulation of co-stimulatory molecules, cytokines, chemokines and allows for heightened dendritic life in vivo. Therefore, decision of tolerance versus immunity is centered, at least in part, on the maturational status of the antigen presenting cell compartment. Appropriate maturation of antigen presenting cells will license them to trigger productive cell-mediated immunity.

The impact of depriving dendritic cells of a maturational signal results in T-cell death, anergy and the emergence of regulatory T-cells ($T^{reg}$) One way of exemplifying what the impact is of immature dendritic cell antigen presentation, is to examine the immune response to self-antigens. In a steady-state, dendritic cells from most lymphoid organs are phenotypically and functionally immature (Wilson, et al. (2004) *Blood* 103:2187-2195), whereas dendritic cells that migrate into the iliac, mesenteric, mediastinal, or subcutaneous lymph nodes from peripheral tissues are mature. Persistent presentation of self-antigens by immature dendritics is a critical factor in maintaining peripheral self-tolerance (Steinman, et al. (2003) *Annu. Rev. Immunol.* 21:685-711). This self-tolerance is induced by the induction of T-cell death, anergy and the emergence of self-reactive $T^{reg}$. In particular, studies show that immature dendritic cells are capable of consuming cell-associated antigens and inducing T-cell anergy or deletion as long as they are not induced to mature via CD40 ligation (Bonifaz, et al. (2002) *J. Exp. Med.* 196:1627-1638; Hawiger, et al. (2001) *J. Exp. Med.* 194:769-779; Scheinecker, et al. (2002) *J. Exp. Med.* 196:1079-1090). It is believed that $CD11c^+$, $CD8\alpha^{hi}$ and not $CD8\alpha^{lo}$, are the dendritic cells that mediate peripheral tolerance. Other means of inducing $T^{reg}$ have also been cited as it has been recently found that in vivo targeting of antigen to immature dendritic cells via DEC205 leads to the expansion of $CD4^+CD25^+$ $CTLA4^+$ regulatory T-cells (Mahnke, et al. (2003) *Trends Immunol.* 24:646-651).

Much like the consumption of self-apoptotic cells, the infusion of allogeneic leukocytes, in the form of donor-specific transfusion (DST), in the presence of CD154 blockade facilitates the presentation of alloantigens by immature dendritic cells resulting in allospecific tolerance. It is well-known that form and biochemical makeup of the self-antigens (and possibly allogeneic antigens) is likely critical to the outcome of the events programmed by immature dendritic cells. It has been shown that the uptake of apoptotic cells by dendritic cells is an effective inducer of T-cell tolerance (Albert, et al. (1998) *Nature* 392:86-89; Inaba, et al. (1998) *J. Exp. Med.* 188:2163-2173), whereas the phagocytosis of necrotic cells has been proven to induce maturation of dendritic cells and development of immunity (Sauter, et al. (2000) *J. Exp. Med.* 191:423-434). The difference resides in the proinflammatory components released by necrotic cells (like heat shock proteins) which result in induction of the innate immune response (Vabulas, et al. (2002) *J. Biol. Chem.* 277:15107-15112; Vabulas, et al. (2002) *J. Biol. Chem.* 277:20847-20853), meanwhile clearance of apoptotic cells by specific cell surface receptors is accompanied by secretion of anti-inflammatory cytokines such as TGF-β (Huynh, et al. (2002) *J. Clin. Invest.* 109:41-50; Golpon, et al. (2004) *FASEB J.* 18 (14):1716-8). In addition, the capacity of necrotic or stressed apoptotic cells to induce dendritic cell maturation is evidenced by the enhanced expression of CD40 and costimulatory molecules, together with heightened IL-12 secretion (Kuppner, et al. (2001) *Eur. J. Immunol.* 31:1602-1609; Zeng, et al. (2003) *Blood* 101:4485-4491). Therefore, tolerance induction by DST inadvertently takes advantage of a pathway that is engineered to induce tolerance to self. DST in clinical practice utilizes whole blood to facilitate transplantation tolerance. While in virtually all mouse studies, spleen cells are used, it has been shown that the infusion of 200 μL of whole mouse blood three times over a period of one week, together with <CD154 induces profound graft tolerance.

Historically, the infusion of whole blood from the donor into graft recipients modestly prolonged allografts in humans (Flye, et al. (1995) *Transplantation* 60:1395-1401; Anderson, et al. (1995) *Transplant Proc.* 27:991-994) and mice (Wood, et al. (1984) *J. Immunol.* 132:651-655). The enhanced graft survival following DST can be substantially lengthened or rendered permanent if the DST is combined with blocking CD154, in both mice and monkeys, indicating the potential clinical relevance of this approach (Preston, et al. (2005) *Am. J. Transplant.* 5:1032-1041; Parker, et al. (1995) *Proc. Natl. Acad. Sci.* 92:9560-9564). Long-term survival of allogeneic kidneys in monkeys that are treated with αCD154, DST and rapamycin has been demonstrated (Kirk, et al. (1997) *Proc. Natl. Acad. Sci. USA* 94:8789-8794; Lin, et al. (1998) *Mol. Cell. Biol.* 18:5523-5532).

It is believed that infused DST rapidly undergoes apoptosis and is presented by host antigen presenting cells and αCD154 may facilitate the apoptosis of the DST by depriving it of a CD40 signal. At the same time, αCD154 impairs the maturation of host antigen presenting cells, committing them to the tolerogenic presentation of DST-derived allopeptides. Delivery of peptides via apoptotic cells appears to be an efficient means to induce peripheral tolerance. In addition, it has been shown that TAP$^{-/-}$ B-cells that are hyperosmotically-loaded with ovalbumin can induce abortive expansion and anergy of ovalbumin-specific cytotoxic T lymphocytes in vivo via indirect presentation (Liu, et al. (2002) *Nat. Med.* 8:185-189). Similarly, antigens expressed on dying pancreatic cells (Coulombe, et al. (1999) *J. Immunol.* 162: 2503-2510) induce tolerance via indirect presentation. Whether targeted via apoptotic cells, or by vectors that target directly to defined dendritic cell surface molecules (like DEC-205), antigens delivered to immature dendritic cells induce profound antigen-specific tolerance, which is amplified in the presence of αCD154.

αCD154-mediated tolerance via cytotoxic deletion of the activated, alloreactive T-cell population has been addressed. It has been shown in mice that (CD154 is ineffective in mice deficient in complement or the common FcR γ chain (Sanchez-Fueyo, et al. (2002) *Transplantation* 74:898-900; Monk, et al. (2003) *Nat. Med.* 9:1275-1280). It has also been shown that aglycosylated αhCD154 (reduced Fc and complement activation) is ineffective in managing graft rejection in primates, yet effective at blocking humoral immune responses (Ferrant, et al. (2004) *Int. Immunol.* 16:1583-1594). Moreover, at higher doses of Fab'2, αCD154 is quite effective at inducing alloreactive T-cell anergy and ablation. Furthermore, the impact of αCD154 on alloreactive T-cell contraction was completely reversed by co-administration of αCD40, suggesting that the T-cells were not eliminated. However, C' and Fc-dependent mechanisms may be operative in this system, but it does not appear to be due to the direct deletion of alloreactive T-cells by αCD154.

Whether graft tolerance is induced by αCD154/DST, non-depleting αCD4 monoclonal antibodies, combinations of αCD154/CTLA-41g, or αCD2/αCD3 monoclonal antibodies, all induce T$^{reg}$ activities that are critical for long-term tolerance (Graca, et al. (2005) *Trends Immunol.* 26:130-135). Early studies described a "dominant" and "infectious" form of tolerance in a variety of allograft tolerance systems (Qin, et al. (1993) *Science* 259:974-977). Using DST and αCD154, it was shown that CD4$^+$ T-cells were critical for long-lived survival of the allograft (Graca, et al. (2000) *J. Immunol.* 165:4783-4786). Subsequent studies in allogeneic bone marrow transplantation and other transplant models implicated an important role of CD4$^+$CD25$^+$ regulatory T-cells (T$^{reg}$) in αCD154-induced graft tolerance (Hara, et al. (2001) *J. Immunol.* 166:3789-3796; Taylor & Namba (2001) *Immunol. Cell Biol.* 79:358-367; Taylor, et al. (2001) *Blood* 98:467-474; Taylor, et al. (2001) *J. Exp. Med.* 193:1311-1318).

Additional evidence substantiating the importance of T$^{reg}$ in long-lived graft tolerance have been provided by reconstitution studies. In these studies, RAG$^{-/-}$ mice were reconstituted with defined CD4$^+$ T-cell populations, treated with DST and αCD154, and evaluated for whether graft tolerance could be induced following skin allograft. Upon reconstitution with only CD4$^+$CD25$^-$, T-cells, DST and αCD154 delayed significantly the rejection of allogeneic skin, but the grafts were ultimately rejected. In this case, the delay was due to extensive clonal abortion of the relevant alloreactive T-cells, however a small frequency remained that eventually rejected the graft. Upon the co-adoptive transfer of CD4$^+$CD25$^+$ T-cells with the CD25 T-cells, permanent graft survival becomes evident. Hence, clonal abortion of the alloreactive CD4$^+$ effectors is incomplete, as there appears to be a CD4$^+$CD25$^-$ population that is resistant to tolerance induction. The co-transfer of T$^{reg}$ can readily silence this residual population.

Natural CD4$^+$CD25$^+$ T$^{reg}$, often referred to as naturally-occurring T$^{reg}$, represents 5-10% of peripheral CD4$^+$ T-cells in naïve mice and humans. It is believed that these cells emerge from the thymus as a consequence of high-affinity interactions with self-antigen, avoiding negative selection and escape to the periphery (Jordan, et al. (2001) *Nat. Immunol.* 2:301-306). The functional regulatory importance of this subset of cells was demonstrated by their critical role in maintaining peripheral tolerance (Takahashi & Sakaguchi (2003) *Int. Rev. Cytol.* 225:1-32; Itoh, et al. (1999) *J. Immunol.* 162:5317-5326; Takahashi, et al. (2000) *J. Exp. Med.* 192:303-310; Kumanogoh, et al. (2001) *J. Immunol.* 166: 353-360; Shimizu, et al. (2002) *Nat. Immunol.* 3:135-142; Kanamaru, et al. (2004) *J. Immunol.* 172:7306-7314; Hori, et al. (2003) *Adv. Immunol.* 81:331-371; Takahashi & Sakaguchi (2003) *Curr. Mol. Med.* 3:693-706; Sakaguchi, et al. (2003) *Novartis Found. Symp.* 252:6-23, 106-114). Subsequent analysis in transplantation systems (Hara, et al. (2001) supra; van Maurik, et al. (2004) *J. Immunol.* 172:2163-2170; Graca, et al. (2000) supra; Taylor, et al. (2001) supra; Waldmann, et al. (2004) *Semin. Immunol.* 16:119-126; Lin, et al. (2002) *Nat. Immunol.* 3:1208-1213) and in autoimmunity and infectious disease (Mayer, et al. (1986) *N. Engl. J. Med.*

314:409-413) demonstrated the important regulatory function of these cells in vivo. Based on the surface phenotype of $T^{reg}$ ($CD45RB^{lo}$, CTLA-4+, GITR+, $CD62L^{hi}$, CD25+), purification strategies have emerged. It appears, however, that the foxhead box P3 transcription factor (Foxp3) may be a specific molecular marker for this lineage (Brunkow, et al. (2001) *Nat. Genet.* 27:68-73; Hori, et al. (2003) *Science* 299:1057-1061; Fontenot, et al. (2003) *Nat. Immunol.* 4:330-336; Khattri, et al. (2003) *Nat. Immunol.* 4:337-342). Mice that report a fluorochrome when Foxp3 is transcriptionally activated have been produced (Fontenot, et al. (2005) *Immunity* 22:329-341; Wan & Flavell (2005) *Proc. Natl. Acad. Sci. USA* 102:5126-5131). Use of the $Foxp3^{GFP/RFP}$ mice (Fontenot, et al. (2005) supra) will facilitate the identification of $T^{reg}$ in vivo.

Functional assessment of $T^{reg}$ has relied extensively on the use of in vitro assays. A commonly used assay to measure $T^{reg}$ activity is the co-culture of $T^{reg}$ with $T^{eff}$, with the measurement of suppression of $T^{eff}$ proliferation. This suppression has been shown to be due to a contact-dependent mechanism and not due to cytokines. It has been shown that the granzyme family of molecules may play an important role in contact-mediated suppression by $T^{reg}$ (Gondek, et al. (2005) *J. Immunol.* 174:1783-1786); $T^{reg}$ can directly kill $T^{eff}$ cells, and thus cell cytotoxicity may play a role in suppression.

In contrast to in vitro studies with $T^{reg}$, in vivo studies have identified a number of important soluble factors in suppression. Recent studies have documented a role of IL-10 and TGFβ in tissue and solid graft tolerance (Quezada, et al. (2003) supra; Quezada, et al. (2004) supra; Graca, et al. (2000) supra; Waldmann, et al. (2004) supra; Kingsley, et al. (2002) *J. Immunol.* 168:1080-1086; Honey, et al. (1999) *J. Immunol.* 163:4805-4810). It has been in systems of co-stimulatory blockade (αCD154, CTLA-4-Ig, αCD4 (non-depleting)) that the role of $T^{reg}$ and these factors have been best illuminated. It has been shown that $T^{reg}$ can suppress the responses of both CD4+ and CD8+ effector T cells in graft rejection (van Maurik, et al. (2004) supra; Lin, et al. (2002) supra). Studies have shown that neutralizing IL-10 using αIL-10 or αIL-10R antibodies abrogate suppression and allow the rejection of skin (Hara, et al. (2001) supra; Kingsley, et al. (2002) supra), although there are studies at odds with this finding (Graca, et al. (2002) *J. Immunol.* 168:5558-5565). A role of IL-10 (but not IL-4) in the immunosuppression of inflammatory bowel disease by $T^{reg}$ has been demonstrated (Graca, et al. (2002) *J. Immunol.* 168:5558-5565). Further evidence of a need for IL-10 in colitis model, not a transplant model, was that $T^{reg}$ from IL-10-/- mice could not suppress colitis (Asseman, et al. (1999) *J. Exp. Med.* 190:995-1004).

TGFβ has also been implicated as an immunosuppressive mediator for $T^{reg}$ (Josien, et al. (1998) *J. Clin. Invest.* 102: 1920-1926). In models of DST-induced tolerance in rats, high levels of TGFβ have been noted (Josien, et al. (1998) supra). In rat cardiac transplant models, neutralization of IL-10 and TGFβ has been shown to alleviate tolerance (Bickerstaff, et al. (2000) *Transplantation* 69:1517-1520). It has also been reported that $T^{reg}$ express surface TGFβ (Nakamura, et al. (2001) *J. Exp. Med.* 194:629-644; Kitani, et al. (2003) *J. Exp. Med.* 198:1179-1188), but later studies using $T^{reg}$ from TGFβ-/- mice or from mice with a dominant-negative TGFβ receptor have questioned the importance of $T^{reg}$ production of TGFβ in suppression (Pennica, et al. (1992) *Biochem.* 31:1134-1141). It has been reported that $T^{reg}$ may induce TGFβ from the host, and in that way mediate graft tolerance. Greater insights into the role of TGFβ have been provided in the Irritable Bowel Disease models where it has been reported that $T^{reg}$ from TGFβ-/- mice suppress colitis, and that $T^{reg}$ likely induce TGFβ liberation and activation from the host (Fahlen, et al. (2005) *J. Exp. Med.* 201:737-746).

In contrast to the naturally-occurring $T^{reg}$, adaptive regulatory T cells ($T_R$) have also been described. $T_R$ arise in the periphery from CD4+CD25- T-cells given particular cytokine environments (notably TGFβ), by presentation of immature dendritic cells or via particular routes of antigen administration (e.g., nasal routes (Chen, et al. (1994) *Science* 265:1237-1240)). As with $T^{reg}$, $T_R$ also must be defined operationally. For practical purposes $T_R$ can be produced by the culture of CD4+CD25- T cells in vitro with TGFβ (Walker, et al. (2003) *J. Exp. Med.* 198:249-258; Zheng, et al. (2004) *J. Immunol.* 172:5213-5221; Zheng, et al. (2004) *J. Immunol.* 172:1531-1539; Horwitz, et al. (2003) *J. Leukoc. Biol.* 74:471-478; Zheng, et al. (2002) *J. Immunol.* 169:4183-4189; Chen, et al. (2003) *Blood* 101:5076-5083), by the over-expression of Foxp3 via retroviral transduction (Hori, et al. (2003) supra), or through selective means of antigen presentation in vitro (Jonuleit, et al. (2000) *J. Exp. Med.* 192:1213-1222; Sato, et al. (2003) *Blood* 101:3581-3589; Hoyne, et al. (2001) *Immunol. Rev.* 182:215-227) or in vivo (Apostolou, et al. (2002) *Nat. Immunol.* 3:756-763). It has also been reported in human systems that the co-culture of $T^{reg}$ with $T^{eff}$ can induce the $T^{eff}$ to become suppressive (Stassen, et al. (2004) *Transplantation* 77:S23-25).

SUMMARY OF THE INVENTION

The present invention is a method for inhibiting regulatory T-cell ($T^{reg}$) functional activities by blocking $T^{reg}$ cell-mediated mast cell activation.

The present invention is also a method for enhancing an immune response to a vaccine. The method involves administering with a vaccine an agent which blocks $T^{reg}$ cell-mediated mast cell activation so that the immune response to the vaccine is enhanced.

A method for increasing cell and humoral immunity in a subject using an agent which blocks $T^{reg}$ cell-mediated mast cell activation is further provided.

BRIEF DESCRIPTION OF THE DRAWINGS

FIG. 2 shows that mast cell-deficient mice are not capable of establishing long-term allograft tolerance.

FIG. 4 shows that $T^{Reg}$ cells produce high levels of IL-9 on activation both in vitro and in vivo.

DETAILED DESCRIPTION OF THE INVENTION

Figure 1A:
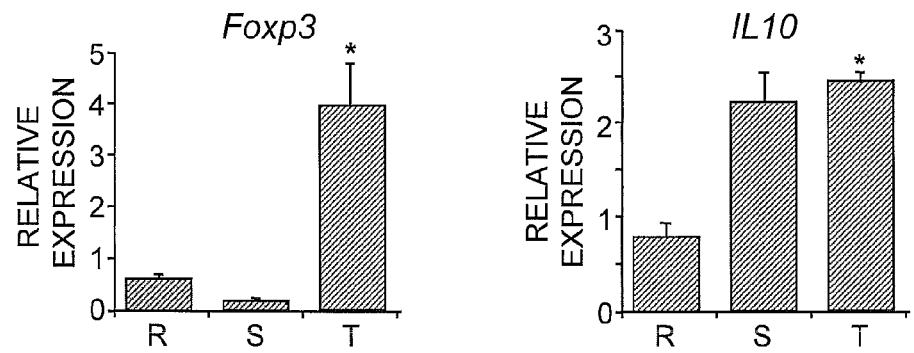
FIG. 1 shows mast cell-related gene expression in tolerant allografts. Infiltrating cells from rejecting (R), syngeneic (S) and tolerant (T) grafts were isolated and quantitative real-time RT-PCR (qRT-PCR) analysis was performed to determine the expression of Foxp3 and Il10 (FIG. 1A).
FIG. 1B shows Granzyme B and Perforin expression, wherein the mRNA levels were normalized to β-actin expression (mean±s.d.).
FIG. 1C shows qRT-PCR analysis of mast cell-related gene mRNA levels in the indicated groups. Data are representative of two individual experiments; values represent the mean±s.d., *P<0.05 (R versus T).
Figure 1B:
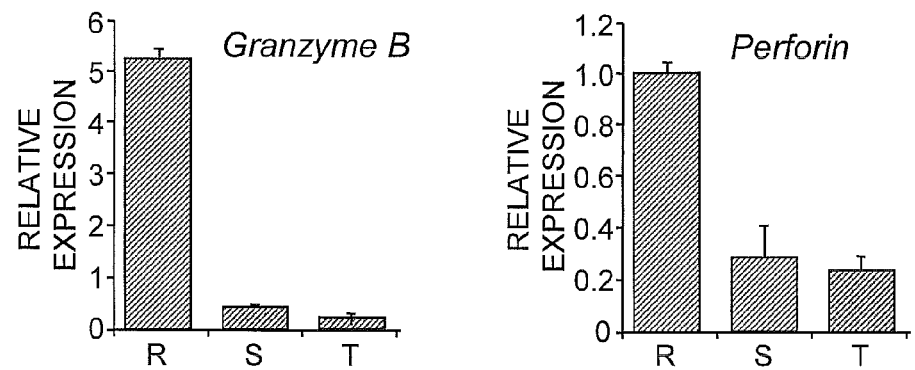
Figure 1C:
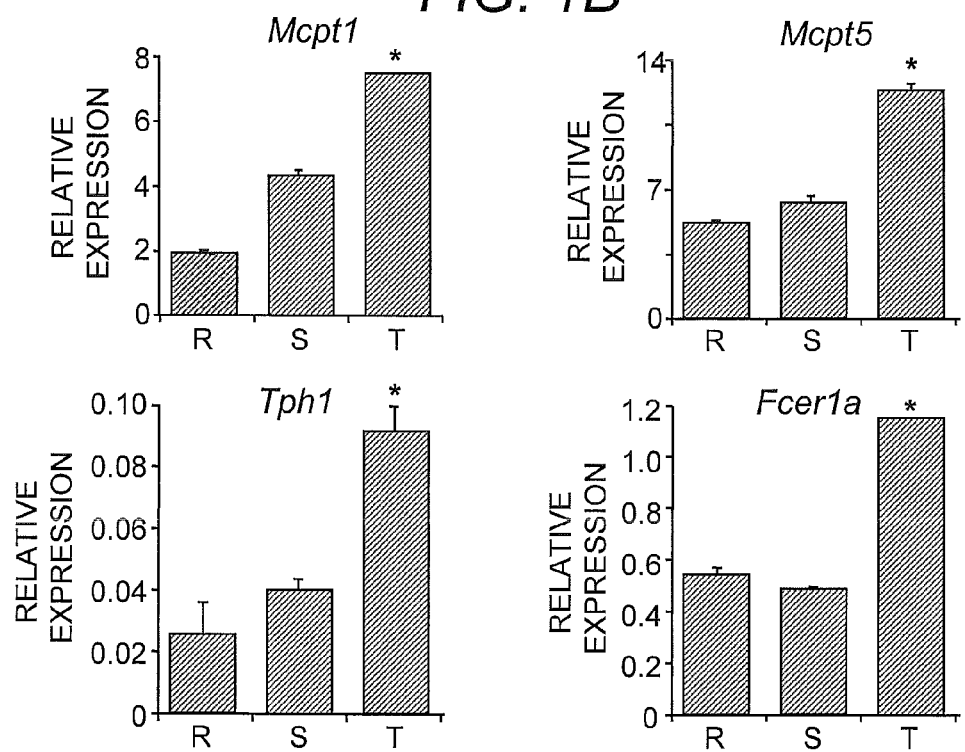

Serial analysis of gene expression (SAGE) in tolerant tissue has shown that genes predominantly expressed by mast cells are overexpressed in cultures of activated $T^{Reg}$ cells and in tolerant allografts (Zelenika, et al. (2001) *Immunol. Rev.* 182:164-179). To determine whether there is an interaction between $T^{Reg}$ and mast cells, the presence of mast cells and their gene products was examined in tolerant allografts in a skin transplantation model. Briefly, mice were rendered tolerant to alloantigens by the intravenous infusion of allogeneic cells (i.e., DST) and concomitant administration of an antibody to CD154 (anti-CD154; Quezada, et al. (2005) *J. Immunol.* 175:771-779). This approach allowed for the long-term acceptance of allogeneic skin grafts compared with the non-tolerant control group, which rejected grafts approximately two weeks after grafting. To compare mast-cell-associated gene expression during graft rejection or tolerance, mice received a second graft (30 days after the first grafting), which was harvested seven days later (Zelenika, et al. (2001) supra). Quantitative analysis of messenger RNAs in the infiltrating cells extracted from skin transplants was subsequently performed. The results of this analysis demonstrated that Foxp3 and Il-10 expression was highly upregulated in the tolerant group (FIG. 1A). This indicated the presence of $T^{Reg}$ cells that were producing immunosuppressive mediators in tolerant tissue (Graca, et al. (2002) *J. Exp. Ned.* 195:1641-1646; Hara, et al. (2001) *J. Immunol.* 166:3789-3796). In contrast, granzyme B and perforin expression in the rejecting group was much higher than in either the syngeneic or tolerant groups, as shown in other allograft models (FIG. 1B; Corti, et al. (2005) *Transplant Proc.* 37:4467-4471). Notably, all mast cell-associated genes examined, including mast cell protease 1 (Mcpt1), mast cell protease 5 (Mcpt5), tryptophan hydroxylase (Tph1) and the high-affinity IgE receptor (Fcer1a), were upregulated in the tolerant group compared with the syngeneic and rejecting groups (FIG. 1C).

The mast cell density in syngeneic, rejecting and tolerant grafts was quantified to determine if the increase in mast cell-gene expression was due to increased mast cell infiltration in tolerant grafts. Immunohistochemical analysis of rejecting primary grafts at day 7 revealed an apparent increase in infiltrating CD4$^+$ T cells relative to that seen in syngeneic or tolerant grafts. In addition, CD117$^+$ mast cells that were present in syngeneic grafts were noticeably absent from rejecting grafts at day 7 (Table 1).

TABLE 1

| | Mast Cells per mm$^2$ | | |
|---|---|---|---|
| Day | Rejecting | Syngeneic | Tolerant |
| 7 | 19.3 ± 18.9 | 85.8 ± 16.4* | 49.0 ± 24.4*† |
| 60 | NA | 77.8 ± 16.8 | 90.9 ± 38.8‡§ |

Data are representative of two individual experiments (n = 3-6 mice per group); values represent the mean ± s.d.
NA, not available.
*P < 0.05 by analysis of variance versus values for Rejecting at day 7.
†P < 0.05 by analysis of variance versus values for Syngeneic at day 7.
‡P = 0.5005 by analysis of variance versus values for Syngeneic at day 60.
§P < 0.05 by analysis of variance versus values for Tolerant at day 7.

It has been shown that skin mast cells can migrate to the regional lymph node following antigen challenge to the skin (Wang, et al. (1998) *J. Clin. Invest.* 102:1617-1626). Therefore, the lack of mast cells in the rejecting allografts could be the result of mast cell migration. However, there was no significant increase in mast cell numbers in the draining lymph nodes in the rejecting group when compared to the syngeneic or tolerant groups (Table 2). Hence, the loss of mast cells in rejecting grafts was unlikely to be due to the inflammation-induced migration of mast cells to the regional lymph node, but rather the direct cytotoxic elimination of mast cells by the host.

TABLE 2

| | Mast Cells per mm$^2$ (mean ± s.d.) | | |
|---|---|---|---|
| Day | Rejecting | Syngeneic | Tolerant |
| 7 | 15.6 ± 5.16 | 16.43 ± 5.57* | 17.28 ± 11.96*# |

*P > 0.05 by analysis of variance versus values for Rejecting at day 7.
P > 0.05 by analysis of variance versus values for Syngeneic at day 7.

In contrast to rejecting grafts, in established tolerant grafts (day 60) there was massive $T^{Reg}$ (CD4$^+$Foxp3$^+$)-cell infiltration (Table 3; Graca, et al. (2002) supra) as well as sustained, or increased, mast cell (CD117$^+$) density (Table 1). The increased presence of mast cells in tolerant versus rejecting grafts was consistent with SAGE results, which was indicative of increased mast-cell gene expression, and the reverse transcription-polymerase chain reaction (RT-PCR) data reported herein. Collectively, these data indicate that both mast cells and $T^{Reg}$ cells increase in number in tolerant allografts and may be crucial in sustaining allograft survival.

TABLE 3

| | Mast Cells per mm² (mean ± s.d.) | |
|---|---|---|
| Day | Syngeneic | Tolerant |
| 60 | 24.48 ± 8.16 | 342.05 ± 86.30* |

*P = 0.004869 by analysis of variance versus values for Syngeneic at day 60. Data are representative from two individual experiments (n = 3~6 mice/group).

Figure 2A:
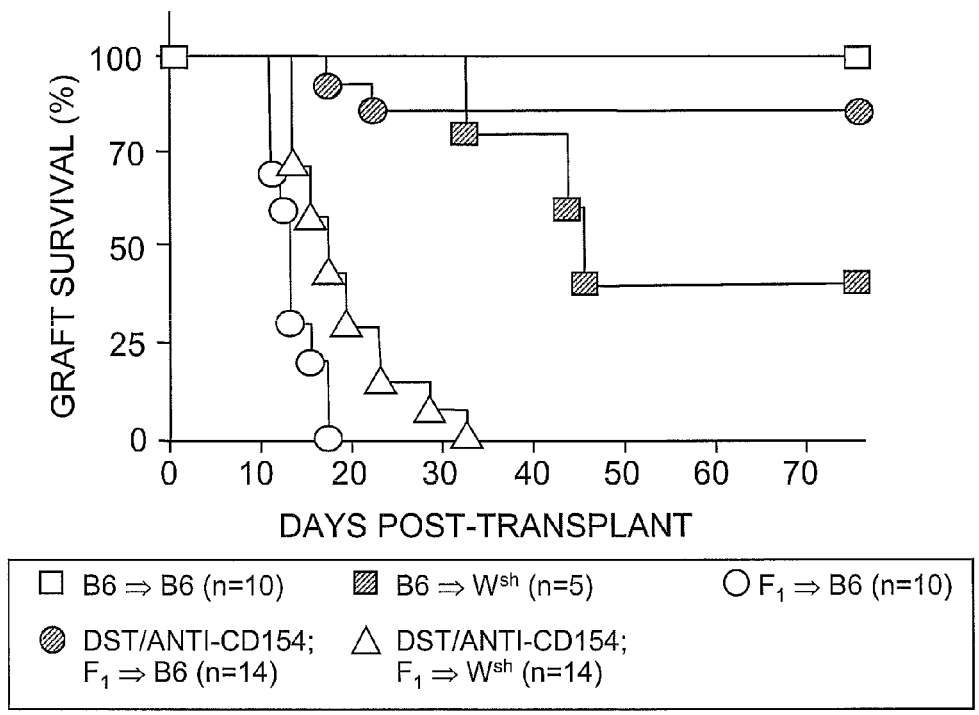
In FIG. 2A, anti-CD154 and DST were co-administered to mast-cell-deficient mice ($W^{sh}$) and allogeneic and syngeneic graft survival in treated $W^{sh}$ and C57BL/6 (B6) mice were followed over time. F1 is a hybrid of C57BL/6 and BALB/c.

Mast cells were functionally implicated in $T^{Reg}$-cell-mediated allograft survival through a series of studies in mast-cell-deficient mice (C57BL/6 $Kit^{W-sh}$; $Kit^{W-sh}$ ($W^{sh}$) mice). $W^{sh}$ mice have an inversion mutation in the transcriptional regulatory elements upstream of the c-Kit open reading frame, which influences c-Kit gene expression in a tissue- and age-specific manner (Galli, et al. (2005) Nature Immunol. 6:135-142; Berrozpe, et al. (1999) Blood 94:2658-2666). Mast cell numbers in $W^{sh}$ mice decrease exponentially after birth owing to their developmental dependence on c-Kit (Yamazaki, et al. (1994) Blood 83:3509-3516; Grimbaldeston, et al. (2005) Am. J. Pathol. 167:835-848), whereas the frequency of other haematopoietic and lymphoid cell populations remains relatively normal. To assess the role of mast cells in allograft survival, $W^{sh}$ mice were administered anti-CD154 and DST to induce allospecific tolerance and grafted with allogeneic skin. Co-administration of anti-CD154 and DST induced long-term acceptance of skin allografts in wild-type mice (median survival time (MST)>70 days), but not in the $W^{sh}$ mice (MST=17 days; P<0.0001; log-rank test; FIG. 2A). In fact, anti-CD154/DST-treated $W^{sh}$ mice rejected allografts at a rapid pace that was almost indistinguishable from the untreated control mice (MST=13 days). Hence, mast cells were essential for anti-CD154/DST-induced tolerance. One of the control groups (syngeneic C57BL/6 skin transplant onto $W^{sh}$ mice) demonstrated delayed rejection (MST=45 days) with long-term survival of 40% of the grafts (FIG. 2A). This delayed rejection could be due to differences in minor histocompatibility molecules in addition to the impaired development of melanocytes in the $W^{sh}$ mice (Yamazaki, et al. (1994) supra). $W^{sh}$ mice express c-Kit in melanocytes at an early age, which should allow the central tolerance to become established; however, the lack of normal melanocyte development in the adult may allow for this minor, delayed rejection response.

Figure 2B:
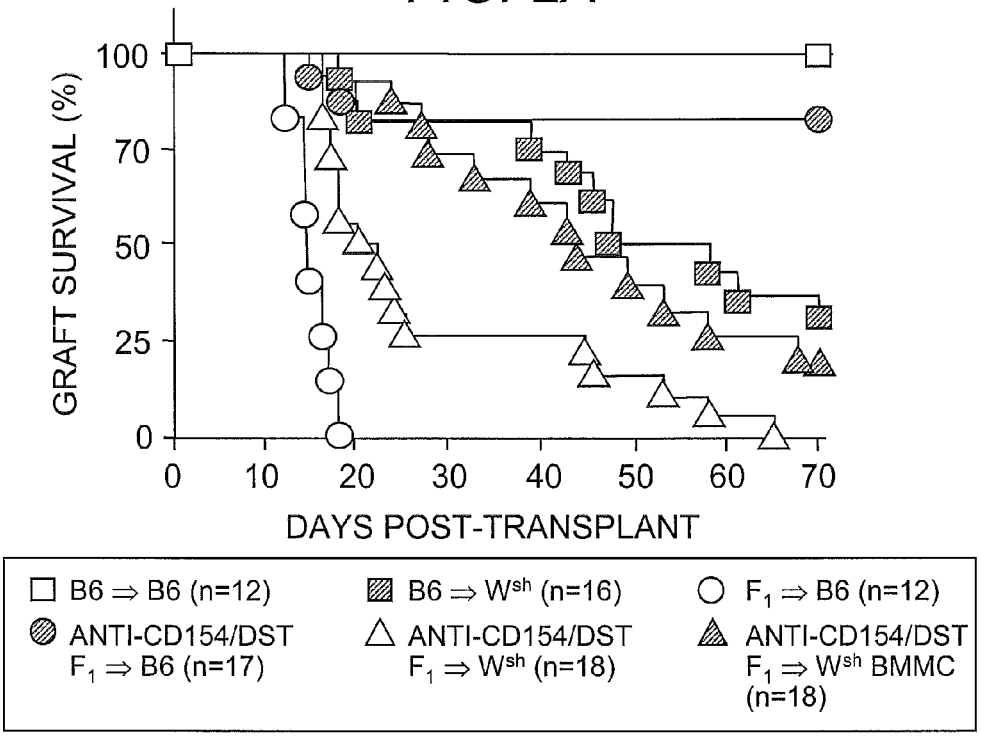
In FIG. 2B, a group of $W^{sh}$ mice received bone-marrow-derived mast cells (BMMCs), subcutaneously, 8 weeks before anti-CD154/DST co-administration and skin grafting. Graft survival was followed over time and compared with the control group without BMMC reconstitution. All skin graft rejection assays were confirmed by at least three individual experiments.

To examine further the role of mast cells in transplantation tolerance, mast cell-knockin mice were prepared (Galli, et al. (2005) Supra). It has been shown that mast cells can be reconstituted both systemically and/or regionally in mast cell-deficient mice by adoptive transfer of bone-marrow-derived mast cells (BMMCs) generated in vitro (Galli, et al. (2005) supra; Grimbaldeston, et al. (2005) supra). BMMCs were harvested five weeks after the initiation of culture, and a total of 5×10⁶ cells (>99% c-Kit⁺FcεRIα⁺) were injected intradermally into the back skin of $W^{sh}$ mice. Eight weeks after intradermal reconstitution, mice showed comparable mast cell frequency in back skin to that observed in wild-type C57BL/6 mice (Grimbaldeston, et al. (2005) supra). BMMC-reconstituted $W^{sh}$ mice were then grafted with skin transplants after anti-CD154/DST co-administration and the acceptance of allografts was monitored over time. As shown in FIG. 2B, local reconstitution of mast cells in the back skin was able to extend graft survival on $W^{sh}$ mice (MST=44 days) that were initially unable to sustain allografts following anti-CD154 and DST treatment (MST=20 days; P=0.0052). Together with the mast cell-reconstitution experiments, these results indicate an indispensable role for mast cells in the establishment of skin transplant tolerance.

Figure 3:
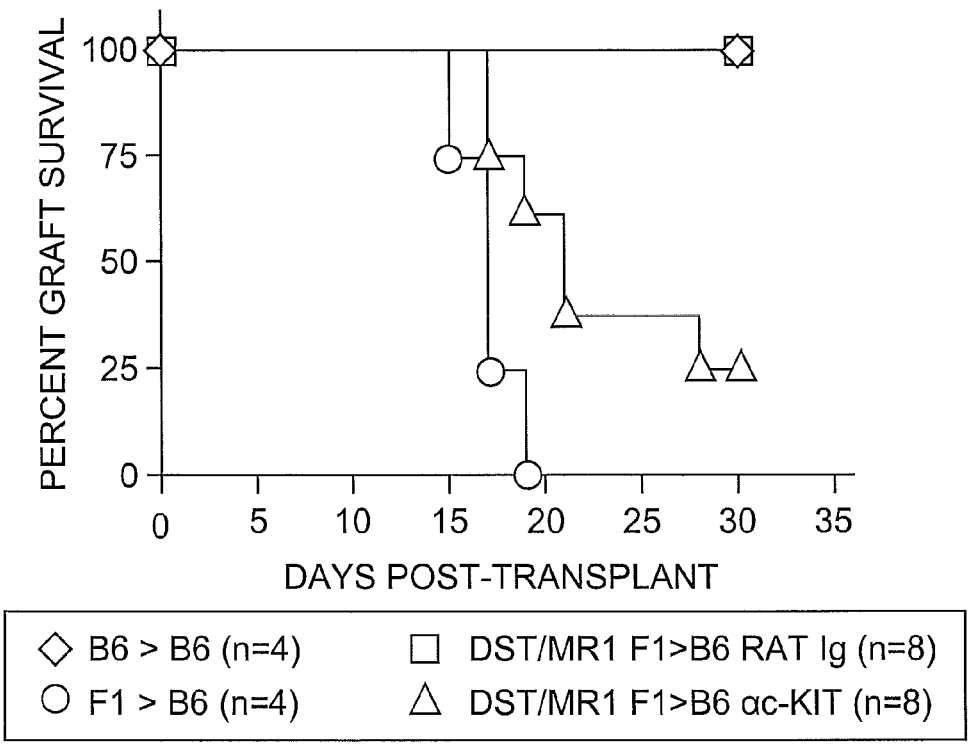
FIG. 3 demonstrates that in vivo depletion of mast cells breaks tolerance and facilitates graft rejection.
Figure 4A:
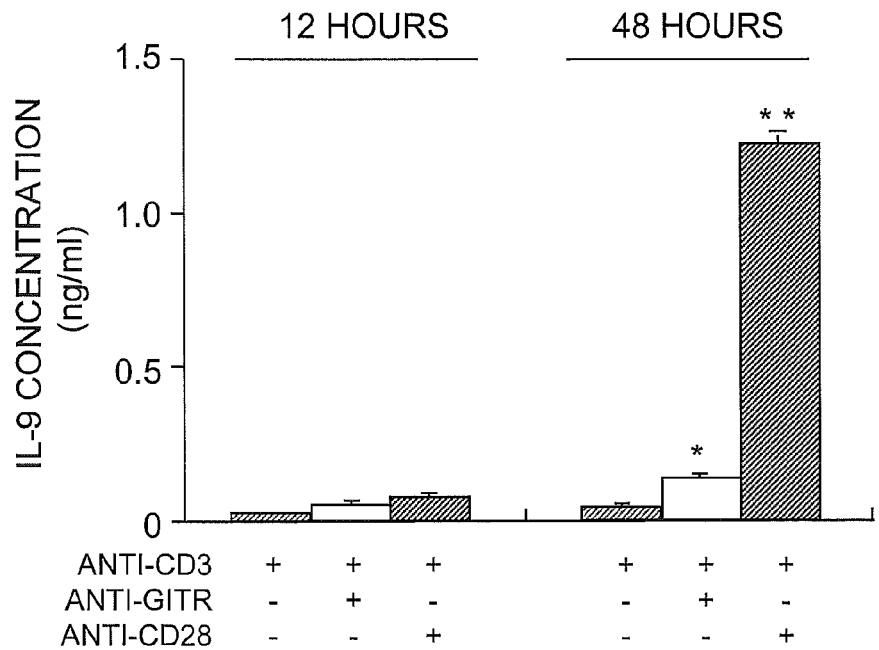
FIG. 4A shows IL-9 concentration in $T^{Reg}$ cell culture supernatant with different treatments for 12 hours and 48 hours. Values represent mean±s.d., *P<0.001 and **P<10$^{-7}$ versus anti-CD3 alone.
Figure 4B:
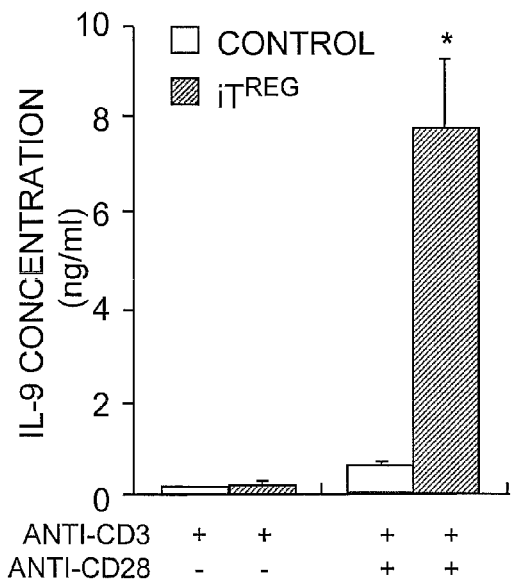
FIG. 4B shows IL-9 production in $iT^{Reg}$ cell culture on activation at 48 hours. Values represent mean±s.d., *P<0.05 versus anti-CD3 alone.
Figure 4C:
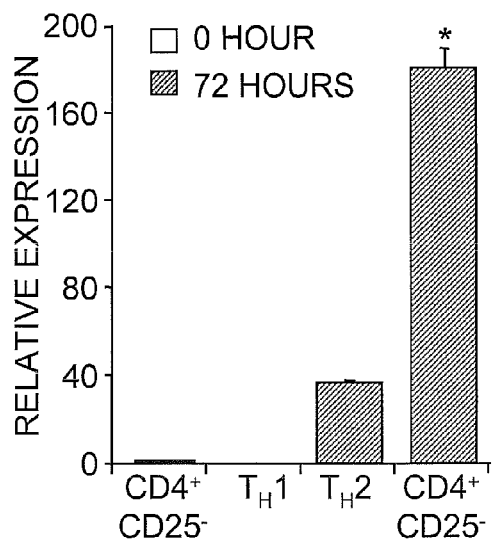
FIG. 4C shows qRT-PCR of IL-9 expression in different T-cell subsets. T-cell subsets were stimulated with anti-CD3 and anti-CD28 for 72 hours. Values represent mean±s.d., *P<0.001 versus $T_H2$ cell culture.

Moreover, in vivo depletion of mast cells using an anti-c-kit antibody breaks tolerance and facilitates graft rejection. Mice were tolerized with anti-CD154 and DST at days −7, −5, −3, and −1 prior to receiving an F1 skin graft. Subsequently, the mice were treated with 100 μg of anti-c-kit or control rat Ig by I.d. injections every three days until the conclusion of the experiment. Mice treated with anti-c-kit, but not control rat Ig rejected their allografts (see FIG. 3). To demonstrate that $T^{Reg}$ and mast cells functionally interact to establish regional tolerance in the tolerant allograft, gene expression patterns were analyzed (See Table 4). Analysis of gene array data from anti-CD3/anti-glucocorticoid-induced tumor necrosis factor-related gene (GITR)-activated $T^{Reg}$ cells indicated that amongst the genes differentially expressed, Il9 was highly upregulated upon $T^{Reg}$-cell activation. IL-9 was initially cloned as a T-cell growth factor whose receptor shares the common γ-chain with IL-2 family members such as IL-2, -4, -7, -15 and -21 (Van Snick, et al. (1989) J. Exp. Med. 169:363-368; Jarnicki and Fallon (2003) Curr. Opin. Pharmacol. 3:449-455). Subsequently, IL-9 was shown to be a mast cell growth factor on the basis of its capacity to enhance the survival of primary mast cells and to induce their production of inflammatory cytokines, mast cell proteases and the high-affinity IgE receptor (FcεRIα) (Zhou, et al. (2001) Respir. Res. 22:80-84). Furthermore, IL-9-deficient mice contain far fewer mast cells than their wild-type littermates (Townsend, et al. (2000) Immunity 13:573-583). It has now been found that following anti-CD3/anti-GITR stimulation, which has an important role in controlling $T^{Reg}$ cell activities (Shimizu, et al. (2002) Nat. Immunol. 3:135-142; Tone, et al. (2003) Proc. Natl. Acad. Sci. USA 100:15059-15064), Il9 was markedly upregulated in $T^{Reg}$ cells, but not the CD4⁺CD25⁻ T-cell population. Upregulation of IL-9 protein expression in $T^{Reg}$ cells was confirmed by an IL-9 enzyme-linked immunosorbent assay (ELISA; FIG. 4A). Moreover, CD28 co-signaling could induce levels of IL-9 production that greatly exceeded those observed with GITR co-signaling (FIG. 4A). IL-9 production seems to be a common feature of $T^{Reg}$ cells because both n$T^{Reg}$ cells (CD4⁺CD25⁺) as well as i$T^{Reg}$ cells produced high levels of IL-9 on activation (FIG. 4B). i$T^{Reg}$ cells are CD4⁺CD25⁻ T cells cultured with anti-CD3 and transforming growth factor β (TGFβ) in vitro (Chen, et al. (2003) J. Exp. Med. 198:1875-1886). CD4⁺CD25⁻ T cells cultured in the absence of TGF-β produced <10% of the IL-9 compared with i$T^{Reg}$ cells (FIG. 4B). As shown in FIG. 4C, T-helper-2 ($T_H2$) cells secreted IL-9 on activation; however, $T^{Reg}$ cells were superior in terms of IL-9 production on a per-cell basis. Notably, although high levels of IL-9 were produced, IL-9 did not seem to have a role in autocrine $T^{Reg}$ cell growth or suppressive activity in vitro as determined by [³H] TdR uptake assays.

Figure 5:
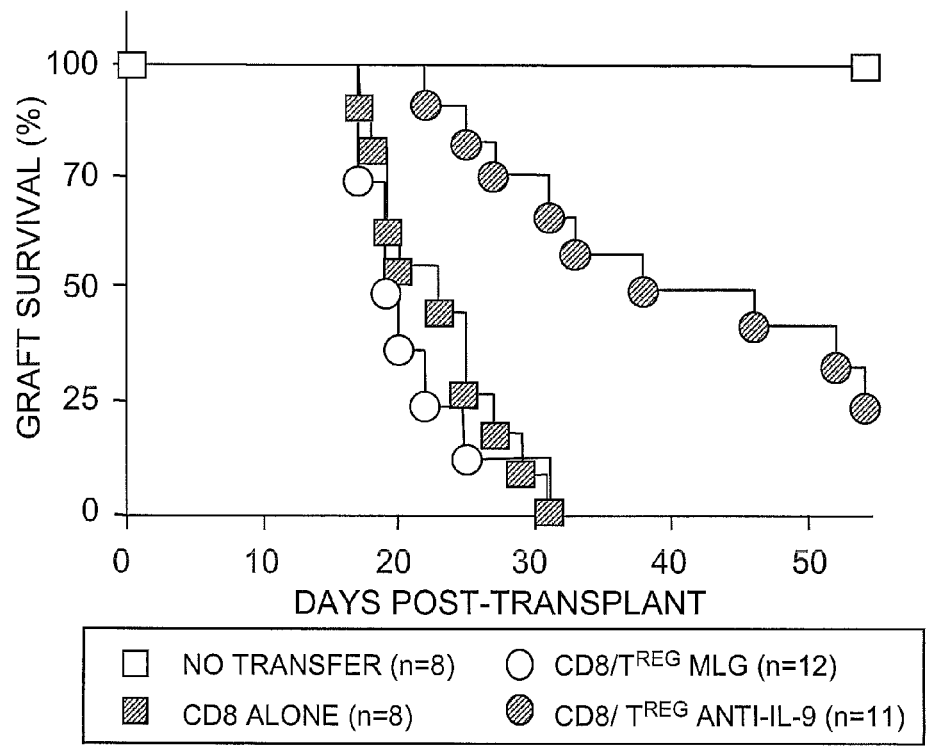
FIG. 5 shows that IL-9 secreted by $T^{Reg}$ cell functionally links mast cells to $T^{Reg}$-cell-mediated allograft tolerance. Rag$^{-/-}$ mice were reconstituted with purified CD8$^+$ T cells with or without $T^{Reg}$ cells at a 5:1 ratio, 1 day before grafting. In the IL-9-treated group, neutralizing anti-IL-9 monoclonal antibody was administered intraperitoneally every other day starting 2 days before grafting. Allograft survival was followed over time and compared with the control group treated with mouse immunoglobulin (mIg). All assays assessing the kinetics of skin graft rejection were confirmed by at least three individual experiments.
Figure 6:
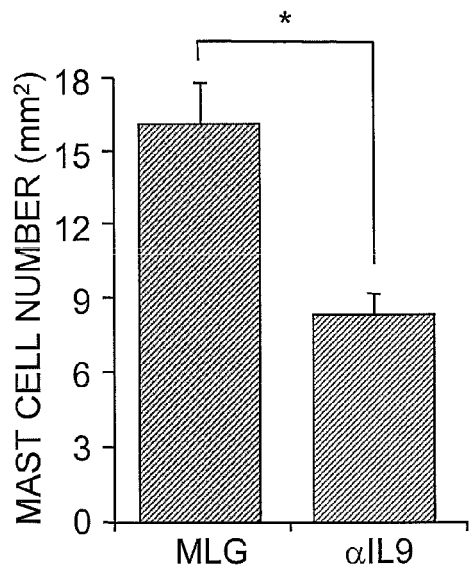
FIG. 6 shows mast cell numbers in Rag$^{-/-}$ mice after αIL-9 administration. Skin transplants from Rag$^{-/-}$ mice were treated with αIL-9 or control mouse Ig (mIg) and stained 10 days post-grafting for CD117$^+$ mast cells. Quantitative analysis of mast cell numbers in skin allografts is shown (*p<0.05).

Given the high levels of IL-9 produced by $T^{Reg}$ cells and the role of IL-9 in mast cell homeostasis, a functional link between IL-9, mast cells and allograft tolerance was examined. First, immunohistochemical and quantitative real-time PCR analysis of skin transplants indicated that IL-9 was detected in tolerant grafts but not in syngeneic grafts. Second, the functional studies in vivo indicated a role for IL-9 in $T^{Reg}$-cell-mediated suppression. To investigate this, neutralizing anti-IL-9 was applied to the anti-CD154/DST skin allograft model described herein. However, only a partial effect was observed with regard to alterations in graft rejection kinetics. Owing to the complexities of the anti-CD154/DST system, which may obscure the potential involvement of IL-9 in $T^{Reg}$-cell-mediated tolerance, a Rag$^{-/-}$ reconstitution system was employed that allowed the use of defined, enriched populations of $T^{Reg}$ cells and effector T cells to study allograft survival (Jarvinen, et al. (2003) *Transplantation* 76:1375-1379). Purified CD8$^+$ T cells were transferred with or without purified CD4$^+$CD25$^+$ T cells into grafted Rag$^{-/-}$ mice. The co-transfer of $T^{Reg}$ cells delayed the onset of graft rejection (MST=42 days) mediated by CD8$^+$ T cells in this model (MST=19.5 days; P=0.0243). The $T^{Reg}$-cell-mediated delay in graft rejection could be completely reversed with anti-IL-9 treatment (MST=23 days; P=0.0161; FIG. 5). As CD8$^+$ T cells did not produce IL-9, and there were no other CD4$^+$ T cells in this system, this approach indicated that IL-9 production by $T^{Reg}$ cells delayed allograft rejection. To ascertain whether anti-IL-9 administration resulted in a reduction of mast cell accumulation to the tolerant grafts, mast cell numbers in various tissues were quantified. A reduced number of mast cells in the skin of mice treated with anti-IL-9 compared with those treated with control-mouse immunoglobulin was observed at day 10 after the transplantation of the allograft into Rag$^{-/-}$ mice (FIG. 6). Hence, the regional production of IL-9 within the tolerant allograft facilitated mast cell accumulation and IL-9 is therefore instrumental in peripheral suppression of alloreactive CD8$^+$ T cells.

Figure 7:
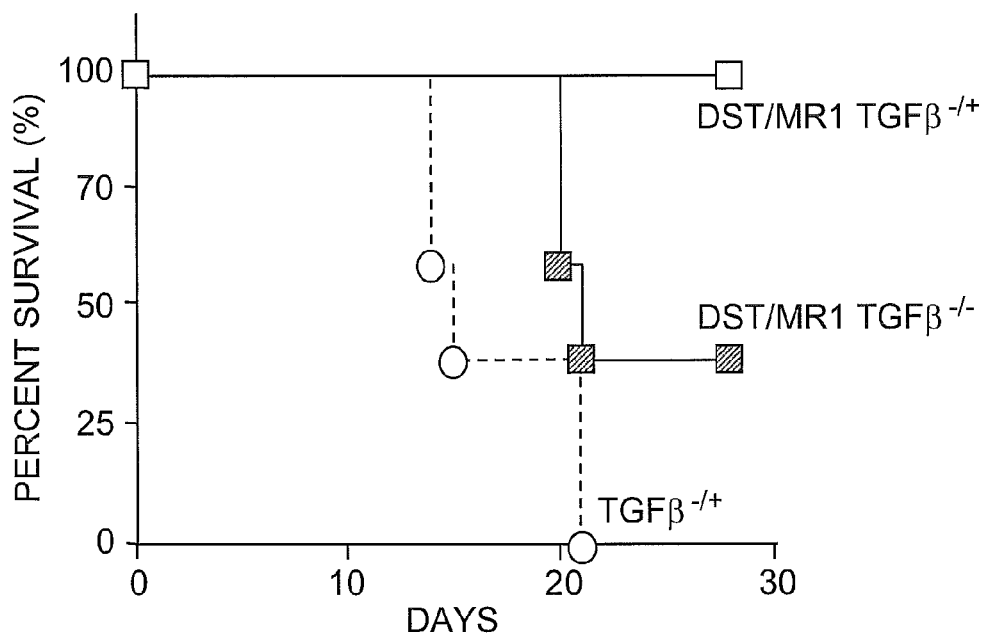
FIG. 7 shows that regional expression of TGFβ is critical in peripheral tolerance of skin allograft.

The data presented herein indicate that $T^{reg}$ cells and their effectors (i.e., IL-9 and mast cells) work regionally to control inflammation in graft tolerance. It has been shown that TGFβ plays an important role in allograft tolerance via $T^{reg}$. However, $T^{reg}$ cells do not have to produce TGFβ themselves, but likely liberate TGFβ from the host (Fahlen, et al. (2005) supra). Thus, to assess the contribution of regional TGFβ production in graft tolerance, mice were tolerized with αCD154/DST and grafted with allogeneic skin from TGFβ$^{+/-}$ or TGFβ$^{-/-}$ mice. By day 20 nearly 50% of the αCD154/DST-treated mice receiving TGFβ-deficient skin had rejected their grafts (FIG. 7). Thus, TGFβ plays an important role regionally in peripheral tolerance-mediated $T^{reg}$ cells.

Figure 8:
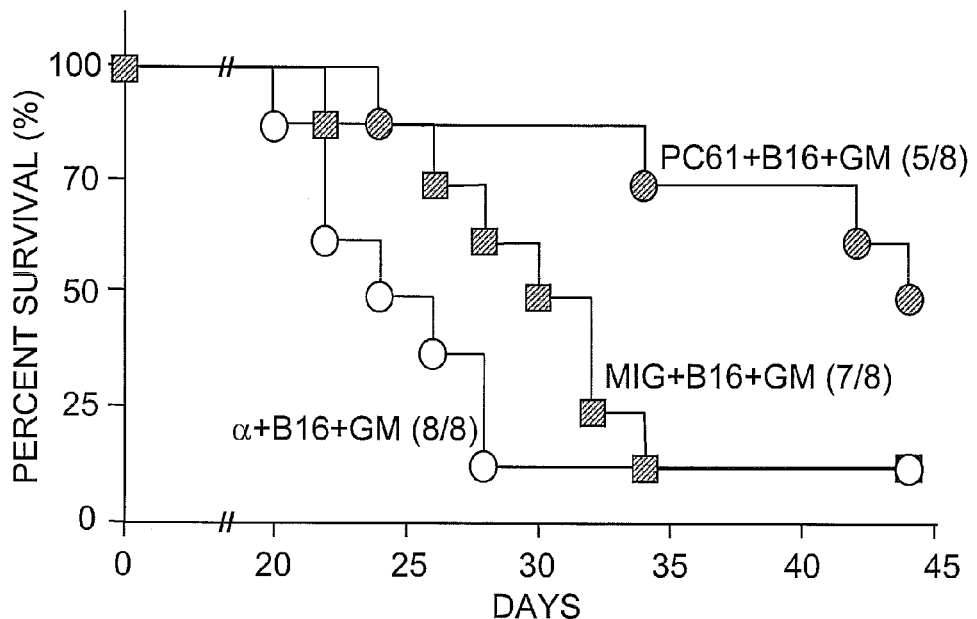
FIG. 8 shows that anti-IL-9 administration delays B16 melanoma growth and prolongs survival. Mice were inoculated with B16 tumors in the right flank and irradiated B16-GMCSF in the left flank. For different treatment groups, anti-CD25 (PC61) was given 4 days prior to tumor challenge; αIL-9 or control mIg was administrated by i.p. injection every other day starting one day before tumor challenge. Survival was followed. Mice were killed when tumor size exceeded 400 mm$^2$.
Figure 9:
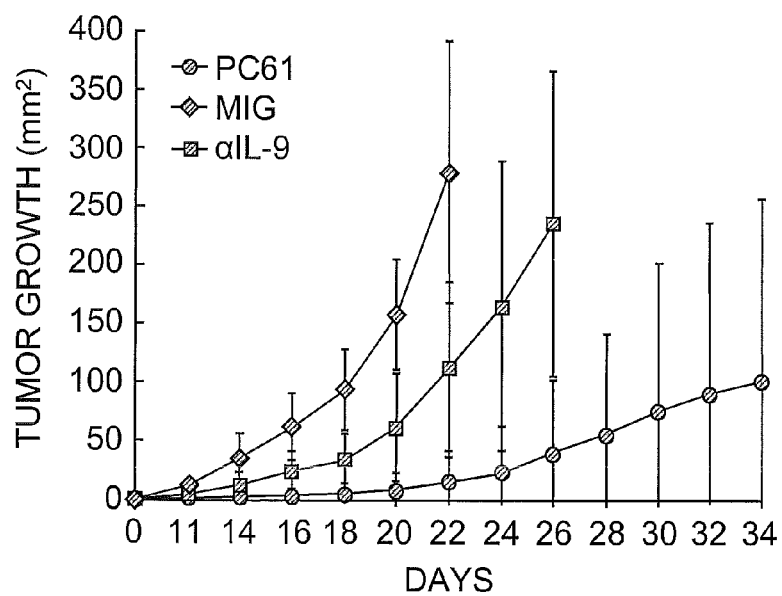
FIG. 9 shows average tumor growth in the treatments indicated. Mice in each group with the biggest and smallest tumors were excluded and average tumor growth was no longer calculated when individual mice in the various treatment groups either died or were sacrificed, in order to exclude the bias introduced into tumor volume calculations with reduced sample size.

It is known that $T^{reg}$ can dampen the immune response to tumors. Hence, agents that can reduce $T^{reg}$ activities should enhance the immune response to tumors and enhance protection of the host to metastatic disease and death. Accordingly, it was determined whether blocking IL-9 could enhance the immune response to tumors. The results of this analysis indicated that αIL-9 alone did not alter the immune response of mice to an autologous melanoma, B16-F10. Tumor growth and mouse survival was unaltered by antibody therapy. It was then determined whether αIL-9 could enhance the immune response in combination with a tumor vaccine. As shown in FIG. 8, αIL-9 increased survival of mice over control mice receiving mIg. Moreover, αIL-9 impaired the growth of the tumor when used in combination with a tumor vaccine (FIG. 9). That is, if mice were first immunized with irradiated B16 vaccine, B16-GM-CSF (a tumor line transduced to express GM-CSF), and given αIL-9 (one day prior to challenge tumor), survival of mice was enhanced over those that received a control mIg. As an additional control, mice were pretreated with αIL25 (PC61; four days prior to tumor challenge) to eliminate $T^{reg}$ prior to tumor challenge. In this case, over 50% of mice had greatly extended survival.

These data demonstrate that IL-9, through mast cell activation, mediates an amplification loop critical for graft tolerance. $T^{reg}$, through the production of IL-9 to activate or recruit mast cells that synthesize and release TGFβ via secretory granules, wherein TGFβ is liberated through the actions of mast cell proteases (Kuppner, et al. (2001) *Eur. J. Immunol.* 31:1602-1609). In addition to mast cell-produced TGFβ, it has been shown that IL-9 strongly up-regulates the production of TGFβ by monocytes (Pilette, et al. (2002) *J. Immunol.* 168:4103-4111). This is consistent with existing data showing that TGFβ-mediated suppression by $T^{reg}$ in vivo is due to host production of TGFβ, and not the intrinsic production by $T^{reg}$ (Fahlen, et al. (2005) supra). Further, the role of mast cells and the litany of products they produce in skewing away from a $T_H1$-oriented inflammatory environment appears to play a role in $T^{reg}$ functional activities.

Accordingly, the present invention is a method for inhibiting $T^{reg}$ cell functional activities by blocking $T^{reg}$ cell-mediated mast cell activation. As used in the context of the present invention, a $T^{reg}$ cell is intended to mean a CD4$^+$ $T^{reg}$ cell, i.e., naturally-occurring $T^{reg}$ or adaptive $T^{reg}$, as opposed to CD8$^+$ $T^{reg}$ cells which have been described (Gilliet & Liu (2002) *J. Exp. Med.* 195:695-704; Zhou, et al. (2001) *J. Immunol.* 167:107-113). Functional activities of the CD4$^+$ $T^{reg}$ cells, which can be effectively inhibited by blocking $T^{reg}$ cell-mediated mast cell activation include, but are not limited to, peripheral tolerance and immune response to tumors.

In accordance with the present invention, $T^{reg}$ cell-mediated mast cell activation is inhibited by contacting a $T^{reg}$ cell with an agent that inhibits the expression or activity of a mast cell-activating factor produced by the $T^{reg}$ cell. While one embodiment of the present invention embraces IL-9 as a mast cell-activating factor produced by $T^{reg}$ cells, it is contemplated that one or more of the $T^{reg}$ cell-produced gene products listed in Table 4 may also be involved in immune suppression via mast cell activation.

TABLE 4

| Gene Name | Fold Change | AFFYMETRIX® Identification Number |
|---|---|---|
| 12-Hour Exposure to αGITR | | |
| CCR6 | 1.94 | 1450357 a |
| Irf4 | 1.89 | 1421173 |
| CXCL10 | 1.83 | 1418930 |
| T-bet | 1.83 | 1449361 |
| IL1R Type 2 | 1.8 | 1419532 |
| NFκB2 | 1.72 | 1425902 a |
| IκBα | 1.65 | 1449731 s |
| TRAF1 | 1.64 | 1423602 |
| Bcl-2like | 1.63 | 1420888 |
| CD30L | 1.51 | 1450272 |
| CCR8 | 1.47 | 1422291 |
| Granzyme B | −2.25 | 1419060 |
| Klrg1 | −1.96 | 1420788 |
| Btg2 | −1.79 | 1448272 |
| IL4 | −1.77 | 1449864 |
| SOCS3 | −1.6 | 1455899 x |
| IL4Rα | −1.6 | 1421034 |
| CD53 | −1.59 | 1448617 |
| IFNγR | −1.58 | 1448167 |
| PDCD4 | −1.57 | 1418840 |
| Gata1 | −1.57 | 1449232 |
| Lfng | −1.53 | 1420643 |
| CCL22 | −1.5 | 1417925 |
| CD150 | −1.48 | 1425570 |
| CTLA4 | −1.33 | 1419334 |
| 48-Hour Exposure to αGITR | | |
| IL-9 | 8.75 | 1450565 |
| CD100 | 2.53 | 1420824 |
| B-Arrestin2 | 2.45 | 1451987 |
| CCL1 | −2.97 | 1421688 |
| Caspase4 | −2.24 | 1449591 |

Positive numbers indicate up regulation. Negative numbers indicate down-regulation.

Inhibition of mast cell activation is intended to include the inhibition of growth, differentiation or recruitment of mast cells which occurs as a result of exposure to one or more cytokines or mast cell-activating factors produced by activated T$^{reg}$ cells.

In accordance with particular embodiments of the present invention, T$^{reg}$ cell-mediated mast cell activation is blocked by inhibiting the expression or activity of one or more mast cell-activating factors produced by T$^{reg}$ cells. In an alternative embodiment, T$^{reg}$ cell-mediated mast cell activation is blocked by inhibiting the binding of the mast cell-activating factor to the mast cell, e.g., using an antibody which binds the mast cell receptor and blocks binding of the mast cell-activating factor or inhibiting the expression of the receptor. In this regard, alternative embodiments of the present invention embrace contacting the mast cell with an agent that inhibits the expression, ligand binding, or signal transduction activity of the receptor that binds the mast cell-activating factor.

As is well-known in the art, a variety of agents can be used to inhibit the expression of a target nucleic acid molecule. For example, expression of mast cell-activating factors can be blocked via antisense RNAs, iRNAs, ribozymes and other similar agents. The design and synthesis of such agents are known to those of skill in the art (see, e.g., Waterhouse, et al. (1998) *Proc. Natl. Acad. Sci. USA* 95(23):13959-13964; Elbashir, et al. (2001) *Nature* 411: 494-498; Rossi (1994) *Current Biology* 4:469-471). In this regard, IL-9 antisense are well-known (see, e.g., Gruss, et al. (1992) *Cancer Res.* 52(4): 1026-31) and shRNA molecules which target human IL-9 nucleic acids (e.g., as disclosed in GENBANK Accession NO. NM_000590) are commercially available from OriGene Technologies, Inc. (Rockville, Md.) and SuperArray BioScience Corp. (Frederick, Md.). Likewise, shRNA molecules which target nucleic acids encoding the human IL-9 receptor (GENBANK Accession No. NM_002186) are well-known and commercially available from sources such as SuperArray BioScience Corp.

Agents useful for inhibiting the activity of a mast cell-activating factor, or receptor thereof, are also known to those of skill in the art and readily available from commercial sources. To illustrate, the effect of IL-9 can be blocked using αIL-9 or αIL-9 receptor antibodies which inhibit binding of IL-9 to its cognate IL-9 receptor. Suitable αIL-9 antibodies are well-known to the skilled artisan (see, e.g., Cheng, et al. ((2002) *Am. J. Respir. Crit. Care Med.* 166(3):409-16; Kung, et al. ((2001) *Am. J. Respir. Cell Mol. Biol.* 25:600-605) and are commercially available from such sources as MedImmune, Inc. (Gaithersburg, Md.). Likewise, exemplary αIL-9 receptor antibodies are commercially available from sources such as BioLegend (San Diego, Calif.).

Inhibition of T$^{reg}$ cell functional activities can be carried out in vitro to further investigate T$^{reg}$ cells and T$^{reg}$ cell-produced mast cell-activating factors in peripheral tolerance. Alternatively, inhibition of T$^{reg}$ cell functional activities can be carried out in vivo to, e.g., enhance immune responses to cancer vaccines and infectious disease vaccines.

For in vivo applications agents of the invention are generally formulated into a pharmaceutically acceptable composition. By way of illustration, an αIL-9 antibody can be formulated with a pharmaceutically acceptable carrier, such as buffered saline; a polyol (e.g., glycerol, propylene glycol, liquid polyethylene glycol and the like); carbohydrates such as glucose, mannose, sucrose or dextrans, mannitol; amino acids such as glycine; antioxidants; chelating agents such as EDTA or glutathione; preservatives or suitable mixtures thereof. In addition, a pharmaceutically acceptable carrier can include any solvent, dispersion medium, and the like which may be appropriate for a desired route of administration of the composition. The use of such carriers for pharmaceutically active substances is known in the art. Suitable carriers and their formulation are described, for example, in Remington: The Science and Practice of Pharmacy, Alfonso R. Gennaro, editor, 20th ed. Lippincott Williams & Wilkins: Philadelphia, Pa., 2000.

Agents that block T$^{reg}$ cell-mediated mast cell activation (e.g., αIL-9 antibodies) can be co-administered to a subject in need of treatment, e.g., prior to, concurrently with, or subsequently after vaccination with a cancer or infectious disease vaccine to enhance the immune response to the vaccine. Routes of administration and dosing can be carried out according to standard medical practices based upon similar agents as well as the condition of the patient and the disease to be prevented or treated. As a component of a vaccine, an agent that blocks T$^{reg}$ cell-mediated mast cell activation can be used in the prevention or treatment of cancers of the prostate, breast, pancreas, colon and rectum, lung, skin, kidney, ovary, bladder, and cervix, as well as lymphoma and leukemia. In particular embodiments, the cancer is an epithelial cancer. By way of illustration, one or more αIL-9 antibodies can be co-administered with glycolipids such as GM2, fucosyl GM1 and globo H and the mucin backbone MUC1 to induce an immune response to cancer cells expressing these antigens (see, e.g., Kagan, et al. (2005) *Cancer Immunol. Immunother.* 54:424-430; Ragupathi, et al. (2005) *J. Immunol.* 174:5706-5712). It is contemplated that modifications in timing of the vaccine and/or dosing of αIL9 could dramatically enhance its efficacy at enhancing anti-tumor immunity. In addition, there may be tumors in which αIL9 in the absence of an overt vaccine may be efficacious. That is, if the tumor itself is immunogenic, αIL9 alone may provide therapeutic benefit.

Likewise, agents disclosed herein for blocking T$^{reg}$ cell-mediated mast cell activation can be used alone or as a component of an infectious disease vaccine to prevent or treat an infectious disease. For example, T$^{reg}$ cells are known to be rapidly induced following blood-stage infection with malaria and are associated with a burst of TGFβ production, decreased proinflammatory cytokine production, and decreased antigen-specific immune responses (Walther, et al. (2005) *Immunity* 23(3):287-96). Thus, by blocking T$^{reg}$ cell-mediated mast cell activation and subsequent TGFβ production, *P. falciparum* rates of parasite growth in vivo can be reduced and immune responses increased. Moreover, as a component of a vaccine, an agent that inhibits the expression or activity of a mast cell-activating factor can facilitate immune responses to bacteria, viruses, parasites and fungi antigens.

Agents that block T$^{reg}$ cell-mediated mast cell activation also find use in a method for increasing cell and humoral immunity in a subject. Such a method involves administration to a subject, at risk of having or having a disease or condition associated with a less than desirable immune response (e.g., to an infection or tumor), a prophylactic or therapeutic agent disclosed herein prior to or after the manifestation of symptoms associated with the disease or condition so that cell and humoral immunity in the subject is increased. Subjects at risk or having a disease that would benefit from treatment with such agents or methods can be identified, for example, by any diagnostic assay known in the art.

The invention is described in greater detail by the following non-limiting examples.

EXAMPLE 1

Expression Profiling

To facilitate comparisons with established expression profiles of $T^{reg}$ cells, standard growth and activation conditions were employed (McHugh, et al. (2002) supra). Briefly, fresh isolated $T^{reg}$ cells (~96% positive) were inoculated at $10^6$/mL into complete RPMI medium supplemented with 10% fetal bovine serum and 100 units IL-2 in a 24-well plate precoated with anti-CD3 with or without anti-GITR (DTA-1) (Shimizu, et al. (2002) supra). The cells were cultured at 37° C. for 0, 12 and 48 hours, RNA was purified and subsequently analyzed using an Affymetrix® mouse genome A430 oligonucleotide array (Affymetrix®, Santa Clara, Calif.).

By comparing the data from resting or activated $CD4^+CD25^+$ T-cell groups, gene expression patterns were found to be similar to those established in the art (Gavin, et al. (2002) supra; McHugh, et al. (2002) supra). To identify genes regulated by GITR signaling, gene expression profiles were compared between the different cell populations with or without anti-GITR treatment.

EXAMPLE 2

Mice

C57BL/6, CB6F1 (hybrid of C57BL/6 and BALB/c), C57BL/6 $Kit^{W-sh}$; $Kit^{W-sh}$ ($W^{sh}$) and C57BL/6 $Rag^{-/-}$ mice were purchased from the Jackson Laboratory (Bar Harbor, Me.). In all skin transplantation experiments, $W^{sh}$ mice were at least 8 weeks old before grafting, to ensure mast cell deficiency (Yamazaki, et al. (1994) supra). All animals were maintained in a pathogen-free facility.

EXAMPLE 3

Skin Grafting and Immunization

Skin grafting was performed following established procedures (Quezada, et al. (2005) *J. Immunol.* 175:771-779). In brief, full-thickness tail skins from $CB6F_1$ ($F_1$) donors were transplanted onto the dorsal area of age-matched C57BL/6 recipients. Seven days before skin grafting, $4 \times 10^7$ T-cell-depleted splenocytes from an $F_1$ donor were transferred into recipients through intravenous injection along with three injections of 250 µg anti-CD154 monoclonal antibody (clone MR-1) on days −7, −5 and −3 to induce allograft tolerance. For $T^{Reg}$ cell depletion, 250 µg of anti-CD25 antibody (clone PC61) was administered through intraperitoneal injection 4 days before skin grafting. For blocking IL-9 activities in vivo, 200 µg of neutralizing anti-IL-9 antibody (clone MM9C1; Khan, et al. (2003) *Infect. Immun.* 71:2430-2438) was administered through intraperitoneal injection every other day throughout the duration of the experiments. Control recipients received identical amounts of mouse immunoglobulin.

EXAMPLE 4

Skin-Infiltrating-Cell Isolation

Skin infiltrating cells were isolated following the modified protocol known in the art (Zelenika, et al. (2001) supra). Briefly, secondary-challenge skin transplants from different groups were removed 7 days after grafting. Skin grafts were then cut into small pieces, followed by trypsin digestion at 37° C. for 1 hour. The remaining pieces were washed with RPMI 1640 medium over nylon mesh. Cell debris was removed by filtration through a 100-µm nylon cell strainer and a 40-µm nylon cell strainer, sequentially. The resulting cell suspension was then washed twice in cold HBSS media and used for further analysis.

EXAMPLE 5

Cell Preparation, BMMC Generation and Cell Reconstitution

Single-cell spleen suspensions were prepared from 8-10-week-old mice. $CD8^+$, $CD4^+CD25^-$ and $CD4^+CD25^+$ T cells were purified by magnetic separation with MACS (Miltenyi Biotec, Auburn, Calif.) according to the manufacturer's instructions. Enriched cell populations and purified cells were phenotypically analyzed by fluorescence-activated cell sorting (FACS). The purity of each population was approximately 90-95%. To generate different T-cell subsets, purified $CD4^+CD25^-$ T cells were cultured with plate-bound anti-CD3 monoclonal antibody (clone 145-2C11) at 10 µg/ml and soluble anti-CD28 monoclonal antibody (clone PV-1) at 1 µg/ml. For $T_H1$ cell preparation, recombinant mouse IL-12 (5.0 ng/ml; PeproTech, Rocky Hill, N.J.) with neutralizing anti-IL-4 monoclonal antibody (10 µg/ml; clone 11B11; BD Pharmingen, San Diego, Calif.) were added; for $T_H2$ cell preparation, recombinant mouse IL-4 (5.0 ng/ml; PeproTech) with neutralizing anti-interferon (IFN)-γ monoclonal antibody (10 µg/ml; clone 37895.11; R&D Systems, Minneapolis, Minn.) were added. Cells were harvested after 5 days of culture and their purities were verified by real-time PCR analysis of lineage-specific gene expression (Tbx21 for $T_H1$ and Gata3 for $T_H2$). For $iT^{Reg}$ Cell preparation, recombinant human TGF-β (1 ng/ml; PeproTech) and human IL-2 (100 U/ml; PeproTech) was added. After 5 days of culture, cells were harvested and their purities were verified by FACS analysis of Foxp3 expression. For mast cell reconstitution, BMMCs were generated by culturing bone marrow cells with IL-3 (20 ng/ml; PeproTech) for 5 weeks as known in the art (Razin (1990) *Methods Enzymol.* 187:514-520; Saitoh, et al. (2000) *Immunity* 12:525-535). The purity was assessed by anti-CD117 (c-Kit) and anti-FcεRIα staining. A total of $5 \times 10^6$ EMMCs were then injected intradermally into the $W^{sh}$ recipients 8 weeks before grafting. For $Rag^{-/-}$ mice reconstitution, $1 \times 10^6$ $CD8^+$ T cells were adoptively transferred through intravenous injection with or without $2 \times 10^5$ $CD4^+CD25^+$ T cells 1 day before grafting.

EXAMPLE 6

Real-Time PCR and Gene Array Analysis

Total RNA from isolated skin-infiltrating cells or different T-cell subsets was purified using the RNeasy system (Qiagen®, Valencia, Calif.). Complementary DNA was then prepared and applied to real-time PCR analysis (SYBR® green; Bio-Rad®, Hercules, Calif.). Relative expression of various gene targets normalized β-actin was calculated as:

(2−(experimental CT−β-actin CT))×1000 where CT is the cycle threshold of signal detection. For gene array analysis, as shown in the literature (Gondek, et al. (2005) *J. Immunol.* 174:1783-1786), RNAs purified from different cell populations with various treatments were analyzed using Affymetrix® mouse genome A430 oligonucleotide arrays.

EXAMPLE 7

Cytokine Secretion Assay and Immunohistology

Secretion of IL-9 was assayed by ELISA. Different T-cell populations ($1\times10^6$) were cultured in 24-well plates pre-coated with 1 µg/ml anti-CD3 (clone 2C11) with or without 10 µg/ml anti-GITR (also known as Tnfrsf18; clone DTA-1) or anti-CD28 (clone PV-1). Supernatants were collected at the time indicated. IL-9 was quantified according to the manufacturer's instructions (Peprotech). For immunohistology, previously grafted skins were snap frozen, cryocut, and acetone-fixed. Slides were blocked with normal mouse serum. Tissue sections were stained for CD4 (clone GK1.5), CD117 (clone 2B8) and Foxp3 (clone FJK.16s). For IL-9 staining, biotinylated rabbit polyclonal anti-mouse IL-9 antibodies (Peprotech) and PE-conjugated streptavidin (eBioscience, San Diego, Calif.) were used. The specificity of IL-9 staining was confirmed by the absence of staining in skin tissue from $Il9^{-/-}$ mice.

What is claimed is:

1. A method for inhibiting regulatory CD4$^+$ T-cell ($T^{reg}$) functional activities comprising contacting CD4$^+$ $T^{reg}$ cells of a subject with breast cancer with a vaccine consisting of
   (a) an anti-IL-9 antibody that inhibits the activity of IL-9,
   (b) a fucosyl GM1 or globo H, and
   (c) a pharmaceutically acceptable carrier; and determining whether there is a decrease in tumor growth or an increase in survival.

* * * * *